(12) United States Patent
Misaka et al.

(10) Patent No.: US 11,439,336 B2
(45) Date of Patent: Sep. 13, 2022

(54) BIOLOGICAL INFORMATION MEASUREMENT SYSTEM AND RECORDING MEDIUM

(71) Applicants: Yoshihiro Misaka, Ishikawa (JP); Hirofumi Morise, Kanagawa (JP); Kiwamu Kudo, Ishikawa (JP)

(72) Inventors: Yoshihiro Misaka, Ishikawa (JP); Hirofumi Morise, Kanagawa (JP); Kiwamu Kudo, Ishikawa (JP)

(73) Assignee: RICOH COMPANY, LTD., Tokyo (JP)

( * ) Notice: Subject to any disclaimer, the term of this patent is extended or adjusted under 35 U.S.C. 154(b) by 423 days.

(21) Appl. No.: 16/589,695

(22) Filed: Oct. 1, 2019

(65) Prior Publication Data
US 2020/0100695 A1   Apr. 2, 2020

(51) Int. Cl.
| | | |
|---|---|---|
| A61B 5/00 | (2006.01) | |
| A61B 5/245 | (2021.01) | |
| A61B 5/055 | (2006.01) | |
| A61B 5/291 | (2021.01) | |

(52) U.S. Cl.
CPC .............. *A61B 5/245* (2021.01); *A61B 5/055* (2013.01); *A61B 5/291* (2021.01); *A61B 5/6803* (2013.01)

(58) Field of Classification Search
CPC ......... A61B 5/245; A61B 5/055; A61B 5/291; A61B 5/6803; A61B 5/064
See application file for complete search history.

(56) References Cited

U.S. PATENT DOCUMENTS

2018/0268588 A1* 9/2018 Shinohara .............. G16H 40/60
2018/0325483 A1* 11/2018 Shinohara .............. A61B 5/369

FOREIGN PATENT DOCUMENTS

| JP | 03-251226 | 11/1991 |
|---|---|---|
| JP | 04-109930 | 4/1992 |
| JP | 04-109932 | 4/1992 |
| JP | 04-226631 | 8/1992 |
| JP | 04-303417 | 10/1992 |
| JP | 2654497 | 5/1997 |
| JP | 2002-336211 | 11/2002 |
| JP | 3907753 | 1/2007 |
| JP | 5712640 | 3/2015 |
| JP | 2015-066043 | 4/2015 |

* cited by examiner

*Primary Examiner* — Joel Lamprecht
(74) *Attorney, Agent, or Firm* — Harness, Dickey & Pierce, P.L.C.

(57) ABSTRACT

A biological information measurement system includes a dewar, a single imaging device, and a hardware processor. The dewar covers a head of a subject and contains sensors that are arranged for detecting biological signals. The single imaging device acquires an image in which three or more reference points and the dewar are captured, the reference points being set in relation to the subject. The hardware processor is configured to: measure brain neural activity of the subject based on the biological signals detected by the sensors; determine positional relationships between the reference points of the subject and the sensors based on the reference points and positional relationship data of the dewar; and re-determine the positional relationships between the reference point of the subject and the sensors, based on images that are acquired by the single imaging device at different times.

20 Claims, 8 Drawing Sheets

BIOLOGICAL INFORMATION MEASUREMENT SYSTEM AND RECORDING MEDIUM

CROSS-REFERENCE TO RELATED APPLICATIONS

The present application claims priority under 35 U.S.C. § 119 to Japanese Patent Applications No. 2018-187819, filed on Oct. 2, 2018, and No. 2019-084725, filed on Apr. 25, 2019. The contents of which are incorporated herein by reference in their entirety.

BACKGROUND OF THE INVENTION

1. Field of the Invention

The present invention relates to a biological information measurement system and a recording medium.

2. Description of the Related Art

There are known magnetoencephalographs that is compliant with magnetoencephalography (MEG) for measuring and analyzing weak bio-magnetic fields that are generated in accordance with human brain neural activity. The magnetoencephalograph is provided with a dewar in which a large number of magnetic sensors are arranged. In the magnetoencephalograph, it is important to determine a positional relationship between the dewar and a head of a subject.

In the light of the importance described above, Japanese Unexamined Patent Application Publication No. 3-251226 discloses a technique in which a generator that generates three-dimensional magnetic fields is installed in a dewar, and a receiver is attached to a subject. Furthermore, a relationship between a coordinate system of the subject and a three-dimensional coordinate system is obtained based on the magnetic fields. Japanese Unexamined Patent Application Publication No. 4-303417 discloses a technique of arranging a three-dimensional magnetic field generator on a dewar, arranging a receiver on a frame that can be imaged, mounting the frame on a head of a subject, and determining a positional relationship between the subject and the dewar. Moreover, Japanese Unexamined Patent Application Publication No. 4-226631 discloses a technique of mounting a light emitting source on each of a subject and a dewar, and determining a relative positional relationship between the subject and a magnetic sensor by a position sensor. Furthermore, Japanese Unexamined Patent Application Publication No. 4-109930 discloses a technique of emitting slit light to a subject and a dewar, capturing an image of a projection line of the slit light by a television (TV) camera to obtain three-dimensional surface shapes of the subject and the dewar, and determining a positional relationship between a head of the subject and a magnetic sensor. Moreover, Japanese Unexamined Patent Application Publication No. 4-109932 discloses a technique of detecting a relative positional relationship between a living body and a magnetic sensor from a stereo image that includes indicator points provided in the dewar and the living body.

However, in the technique disclosed in Japanese Unexamined Patent Application Publication No. 3-251226, the magnetic field receiver may be dismounted due to motion of the head of the subject during measurement of brain neural activity and the magnetic fields generated by the magnetic field generator may have adverse effects on measurement of brain neural activity. Thus, it is difficult to simultaneously measure a position and a posture of the head during measurement of brain neural activity. In the technique disclosed in Japanese Unexamined Patent Application Publication No. 4-303417, the frame may be displaced due to motion of the head. Further, each of subjects has a different head shape, so that it is difficult to individually prepare the frame. Even if the frame is stretchable in accordance with the head shape of the subject, it is still difficult to avoid uncomfortable feelings that the head is tightened, and this may result in a disturbing signal for brain neural activity. In the technique disclosed in Japanese Unexamined Patent Application Publication No. 4-226631, similarly to the technique of mounting the magnetic generator and the magnetic receiver, the light emitting source may be dismounted due to motion of the head, so that it is difficult to determine the positional relationship between the dewar and the subject in real time during measurement of brain neural activity. In the technique disclosed in Japanese Unexamined Patent Application Publication No. 4-109930, there is a risk that laser light may enter eyes of the subject. Further, the laser light is scattered by a skin surface, so that a width of the projection line is increased and it becomes difficult to accurately measure a three-dimensional shape of the head of the subject. Japanese Unexamined Patent Application Publication No. 4-109932 discloses the technique that enables to determine the positional relationship between the dewar and the head of the subject even when the head of the subject moves during measurement of brain neural activity. However, in this technique, the positional relationship between the subject and the dewar is determined by a stereo camera, and the dewar moves and sequentially scans measurement points, so that it is difficult to simultaneously measure brain neural activity in the whole head.

Meanwhile, by forming the dewar in a helmet shape, it becomes possible to determine in real time the positional relationship between the head of the subject and the dewar and to measure brain neural activity in the whole head. However, in this case, the head of the subject is hidden behind the dewar, so that it is necessary to reduce a distance between cameras of the stereo camera. Therefore, according to the measurement principle of the stereo camera, a problem may arise such that a measurement error in a depth direction of the head of the subject and the dewar is increased and positioning accuracy is reduced.

SUMMARY OF THE INVENTION

According to one aspect of the present disclosure, a biological information measurement system includes a dewar, a single imaging device, a memory, and a hardware processor coupled to the memory. The dewar covers a head of a subject and containing a plurality of sensors that are arranged for detecting biological signals. The single imaging device is configured to acquire an image in which three or more reference points and the dewar are captured, the reference points being set in relation to the subject. The hardware processor is configured to: measure brain neural activity of the subject based on the biological signals detected by the plurality of sensors; determine positional relationships between the reference points of the subject and the plurality of sensors based on the reference points and positional relationship data of the dewar; and re-determine the positional relationships between the reference points of the subject and the plurality of sensors, based on images that are acquired by the single imaging device at different times.

BRIEF DESCRIPTION OF THE DRAWINGS

The accompanying drawings are intended to depict exemplary embodiments of the present invention and should not be interpreted to limit the scope thereof. Identical or similar reference numerals designate identical or similar components throughout the various drawings.

DESCRIPTION OF THE EMBODIMENTS

Figure 1:
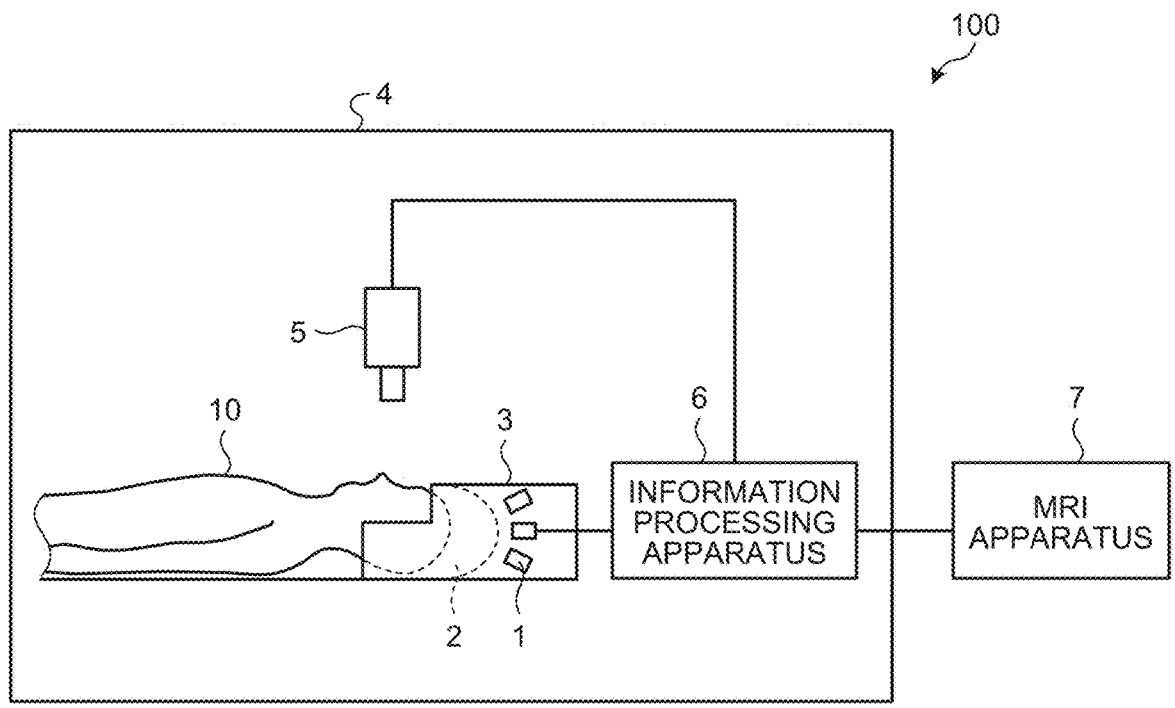
FIG. 1 is a diagram illustrating an example of a system configuration of a biological information measurement system according to a first embodiment.

The terminology used herein is for the purpose of describing particular embodiments only and is not intended to be limiting of the present invention.

As used herein, the singular forms "a", "an" and "the" are intended to include the plural forms as well, unless the context clearly indicates otherwise.

In describing preferred embodiments illustrated in the drawings, specific terminology may be employed for the sake of clarity. However, the disclosure of this patent specification is not intended to be limited to the specific terminology so selected, and it is to be understood that each specific element includes all technical equivalents that have the same function, operate in a similar manner, and achieve a similar result.

An embodiment of the present invention will be described in detail below with reference to the drawings.

The present invention has been conceived in view of the foregoing situations, and an object of the present invention is to enable a single imaging device to acquire an image for correcting a position of a head.

Embodiments of a biological information measurement system and a recording medium according to the present disclosure will be described below with reference to the accompanying drawings.

First Embodiment

FIG. 1 is a diagram illustrating an example of a system configuration of a biological information measurement system 100 according to a first embodiment. As illustrated in FIG. 1, the biological information measurement system 100 includes a biological information measurement apparatus 4 and a magnetic resonance imaging (MRI) apparatus 7 that captures an MRI image. The biological information measurement apparatus 4 includes a brain function measurement apparatus 3, an image acquisition apparatus 5, and an information processing apparatus 6.

The brain function measurement apparatus 3 is a magnetoencephalograph that measures a magnetoencephalography (MEG) signal and an electroencephalography (EEG) signal. A subject 10 as a measurement target puts his/her head into a dewar 2 of the brain function measurement apparatus 3 while wearing electrodes (or sensors) for measuring electroencephalography on the head. The dewar 2 is a helmet-type sensor-housed dewar that surrounds almost the whole area of the head of the subject 10. The dewar 2 is a container in a cryogenic environment using liquid helium, and a large number of magnetic sensors 1 for measuring magnetoencephalography are arranged inside the dewar 2. The brain function measurement apparatus 3 collects electroencephalography signals from the electrodes and magnetoencephalography signals from the magnetic sensors 1. The brain function measurement apparatus 3 outputs the collected biological signals to the information processing apparatus 6.

In general, the dewar 2 with the built-in magnetic sensors 1 is arranged in a magnetic shielding room, but the magnetic shielding room is not illustrated for convenience of illustration.

The information processing apparatus 6 displays waveforms of the magnetoencephalography signals obtained from the plurality of magnetic sensors 1 and waveforms of the electroencephalography signals obtained from the plurality of electrodes on the same time axis in a synchronous manner. The electroencephalography signals are signals that represent electrical activity of nerve cells (the flow of ionic charge that occurs in neuronal dendrites during synapse transmission) by a potential difference between the electrodes. The magnetoencephalography signals are signals that represent minute magnetic field variation that occurs due to electrical activity of the brain. The brain's magnetic field is detected by a high-sensitive superconducting quantum interference device (SQUID) sensor.

Further, the information processing apparatus 6 inputs a tomographic image (MRI image) of the head of the subject 10 imaged by the MRI apparatus 7. The MRI apparatus 7 captures images before or after the brain function measurement apparatus 3 performs magnetic measurement, and the captured image data is sent online or offline to the information processing apparatus 6.

Note that, a tomographic image capturing apparatus that captures a tomographic image of the head of the subject is not limited to the MRI apparatus 7. Alternatively, it may be possible to use an X-ray computed tomography (CT) device.

Figure 2:
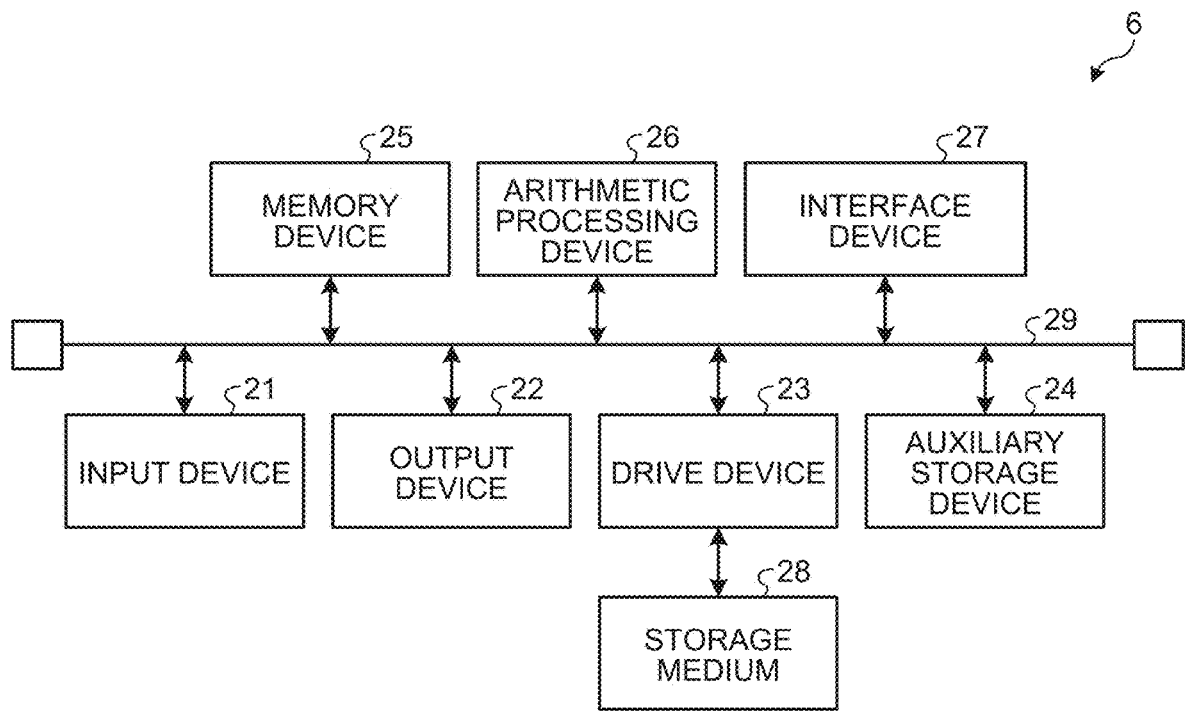
FIG. 2 is a diagram illustrating a hardware configuration example of an information processing apparatus.

The information processing apparatus 6 will be described in detail below. FIG. 2 is a diagram illustrating a hardware configuration example of the information processing apparatus 6.

The information processing apparatus 6 includes an input device 21, an output device 22, a drive device 23, an auxiliary storage device 24 for storing a biological information measurement program, a memory device 25, an arithmetic processing device 26, and an interface device 27, all of which are connected to one another via a bus 29.

The input device 21 is a device for inputting various kinds of information, and is implemented by, for example, a keyboard, a pointing device, or the like. The output device 22 is a device for outputting various kinds of information, and is implemented by, for example, a display or the like.

The interface device 27 includes a local area network (LAN) card or the like and is used for connection to a network.

The biological information measurement program is at least part of various programs that is executed for controlling the information processing apparatus 6. The biological information measurement program is provided by, for example, distribution of a storage medium 28, downloading from a network, or the like. As the storage medium 28 for storing the biological information measurement program, various types of storage media may be used. For example, a storage medium, such as a compact disc read only memory (CD-ROM), a flexible disk, or a magneto-optical disk, that electrically or magnetically stores therein information, a semiconductor memory, such as a ROM or a flash memory, that electrically stores therein information, or the like may be used.

Further, when the storage medium 28 in which the biological information measurement program is recorded is set in the drive device 23, the biological information measurement program is installed in the auxiliary storage device 24 from the storage medium 28 via the drive device 23. The biological information measurement program downloaded via a network is installed in the auxiliary storage device 24 via the interface device 27.

The auxiliary storage device 24 stores therein the installed biological information measurement program, and further stores therein necessary files, data, and the like. The memory device 25 reads the biological information measurement program from the auxiliary storage device 24 and stores therein the biological information measurement program when the information processing apparatus 6 is activated. The arithmetic processing device 26 implements various processes described below in accordance with the biological information measurement program stored in the memory device 25.

Figure 3:
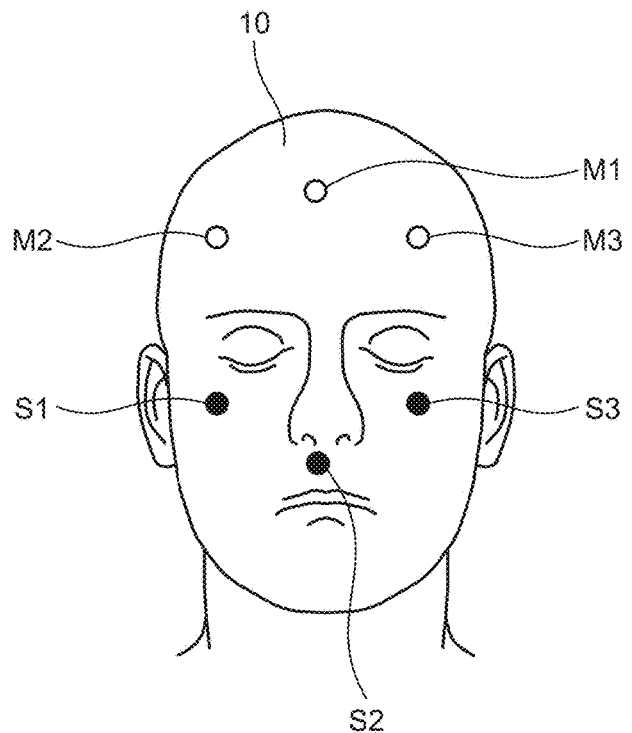
FIG. 3 is a diagram schematically illustrating a head of a subject.

FIG. 3 is a diagram schematically illustrating the head of the subject 10. As illustrated in FIG. 3, three or more marker coils (magnetic generators) are attached to the head of the subject 10 as a measurement target. In the present embodiment, marker coils (magnetic generators) M1, M2, and M3 are attached.

Figure 4:
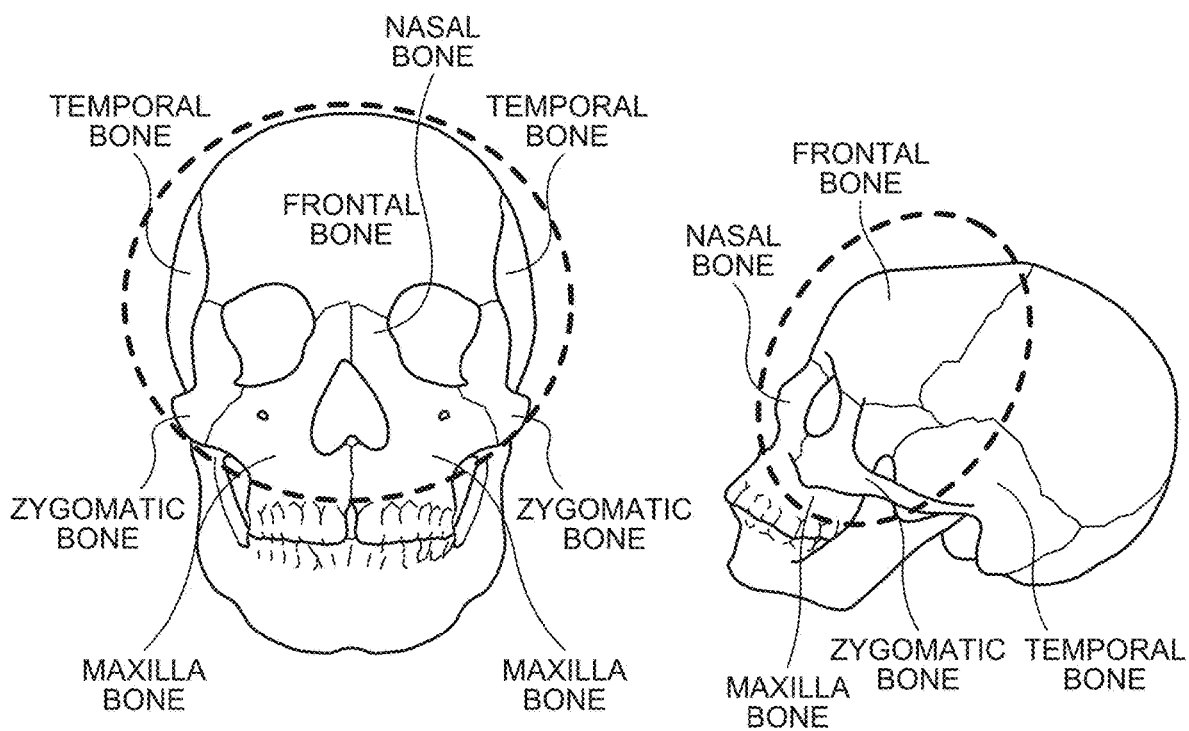
FIG. 4 is a diagram schematically illustrating setting positions of head reference points.

In addition, three or more head reference points as reference points are set on the head of the subject 10. FIG. 4 is a diagram schematically illustrating setting positions of the head reference points. As illustrated in FIG. 4, it is preferable that the head reference points are set at any of positions on the skin over a maxilla bone, a frontal bone, a nasal bone, a zygomatic bone, and a temporal bone. These positions are located on the scalp that can be imaged by the image acquisition apparatus 5 (to be described later) with less affection by motion of the head due to mastication, and allow the head reference points to be stably extracted from an image.

The head reference points may be feature points of the head of the subject 10. For example, corners of eyes, eyebrows, a nasal point, an outline of a cheek or a chin, ears, and the like may be adopted. In those cases, it is possible to perform operation of the present embodiment without physically attaching objects indicating the head reference points onto the head of the subject 10. Thus, it is possible to reduce load of the subject 10 and man-hours for attachment operation.

Alternatively, it may be possible to place marks on the feature points as the head reference points on the head of the subject 10 with an oil-based pen or the like. In this case, it is possible to improve extraction accuracy of the feature points on the head of the subject 10 in the image.

Figure 5:
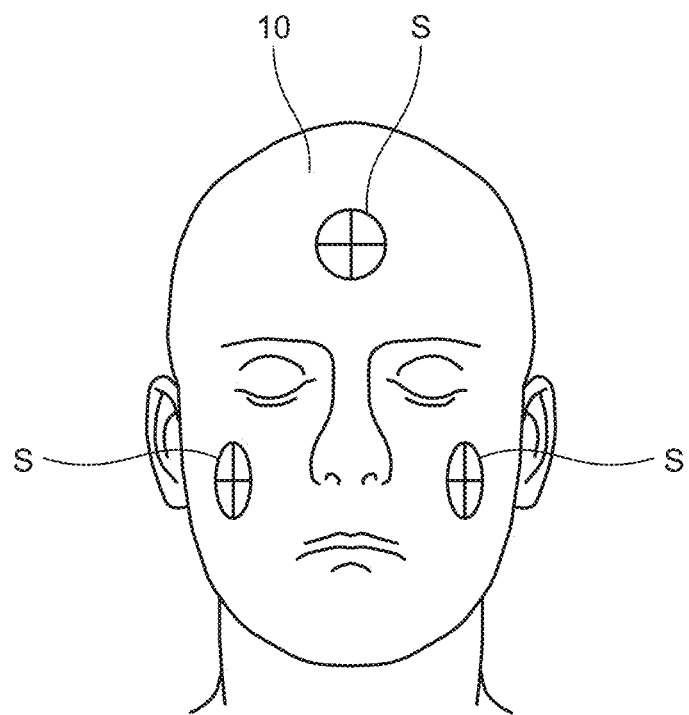
FIG. 5 is a diagram illustrating an example in which seals are attached to the head reference points.

Furthermore, it may be possible to attach seals, as the marks, having known dimensions to the head reference points. FIG. 5 is a diagram illustrating an example in which seals are attached to the head reference points. As illustrated in FIG. 5, when seals S are attached to the head reference points, it becomes possible to easily extract the head reference points on the head of the subject 10 in the image. It is also possible to acquire more detailed information on a curvature of the head of the subject 10 and an image depth direction by using an aspect ratio in the image. Thus, it is possible to improve accuracy of the positional relationship between the magnetic sensors 1 of the dewar 2 and the head of the subject 10. With this configuration, it is possible to improve estimation accuracy of a brain region in which brain neural activity has occurred.

In the present embodiment, as illustrated in FIG. 3, seals S1, S2, and S3 are attached, as the head reference points, to a subnasale and both cheeks on the head of the subject 10.

Alternatively, it is possible to use the marker coils M1, M2, and M3 as the head reference points.

When measurement is performed by the brain function measurement apparatus 3, the information processing apparatus 6 calculates positions of the marker coils in a three-dimensional space of the dewar 2 based on magnetic fields generated by the marker coils detected by the magnetic sensors 1. The information processing apparatus 6 determines the positional relationship between the head of the subject 10 and the magnetic sensors 1 in the three-dimensional space based on pre-provided three-dimensional arrangement data of the magnetic sensors 1 (data representing positions at which the magnetic sensors 1 are arranged). The three-dimensional arrangement data of the magnetic sensors 1 is dewar structural data (positional relationship data) related to the positions and postures of the magnetic sensors 1. Thus, it is possible to obtain the positions of the head reference points by respective coordinate systems, and it is possible to obtain a transformation matrix between the coordinate systems.

In addition, the information processing apparatus 6 accurately measures the positional relationships between the brain of the subject 10 and the magnetic sensors 1 by using the image acquisition apparatus 5.

As described above, the biological information measurement system 100 is configured to cause the magnetic sensors 1 to detect signals generated by brain neural activity of the subject 10. Alternatively, it may be possible to use an optically pumped atomic magnetometer (OPAM) or the like. Furthermore, while the biological information measurement system 100 is configured to cause the magnetic sensors 1 to detect signals generated by brain neural activity of the subject 10, embodiments are not limited thereto. It is sufficient that the biological information measurement system 100 includes a sensor for detecting signals generated by brain neural activity, and a less-invasive sensor, or more preferably, a non-invasive sensor is used to accurately measure vital functions of the subject 10. Examples of the sensor include, in addition to the magnetic sensor, an electroencephalography sensor (voltage sensor), and an optical topography (near-infrared light sensor).

Moreover, the magnetic sensors 1 of the present embodiment may include a plurality of kinds of sensors described above. In this case, however, it is necessary that operation of one of the sensors does not affect measurement performed by the other sensors. In particular, when a magnetic sensor is used as one of the sensors, it is possible to acquire signals generated by a living body even when the living body and the magnetic sensor are not in contact with each other, and therefore, a measurement result is not affected by a sensor attachment state. Therefore, the magnetic sensors 1 are preferable as an embodiment of the present disclosure.

Figure 7:
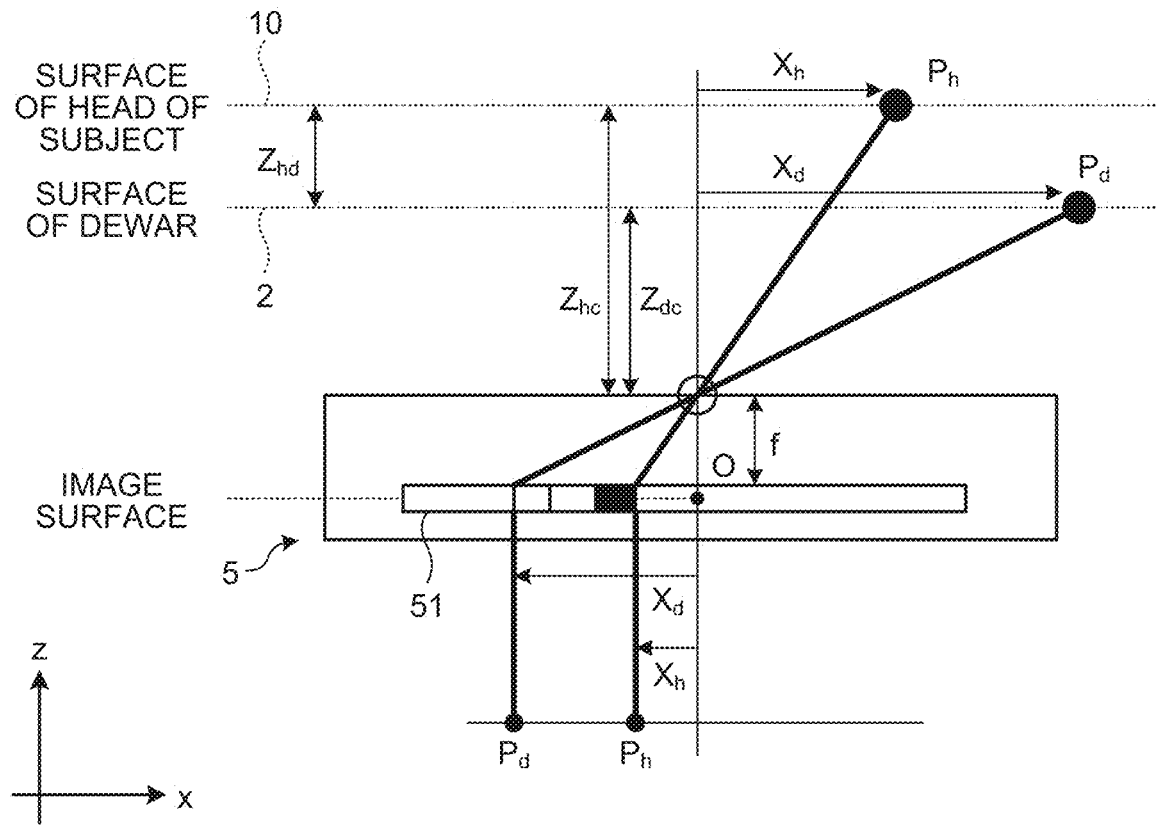
FIG. 7 is a diagram for explaining a method of measuring a distance in the depth direction by using a single camera.

The image acquisition apparatus 5 is provided with, as a single imaging device, a camera 51 (see FIG. 7). It is sufficient that the camera 51 is able to capture a range covering the dewar and the reference points and is a monocular camera, for example. While the brain function measurement apparatus 3 measures magnetoencephalography or the like, the image acquisition apparatus 5 acquires an image in which the head reference points (seals S1, S2, and S3) and the dewar 2 are captured. While details will be described later, the information processing apparatus 6 is able to determine the positional relationships between the head of the subject 10 and the magnetic sensors 1 based on the dewar 2, the head reference points (seals S1, S2, and S3), and the like in the image. Therefore, even if the head of the subject 10 moves during measurement of magnetoencephalography by the brain function measurement apparatus 3, the information processing apparatus 6 is able to determine the positional relationships again. According to the present embodiment, it is possible to determine the positional relationship between the head of the subject 10 and the dewar 2 in real time, and simultaneously measure brain neural activity in the whole head.

Next, a method of measuring a distance in the depth direction by the camera 51 included in the image acquisition apparatus 5 will be described below.

Before describing the method of measuring the distance in the depth direction by a single camera, a method of measuring a distance in the depth direction using a stereo camera (two cameras) will be described.

The stereo camera acquires a target image by using two cameras, and measures a distance in the depth direction based on disparity between feature points that appear in obtained two images.

Figure 6:
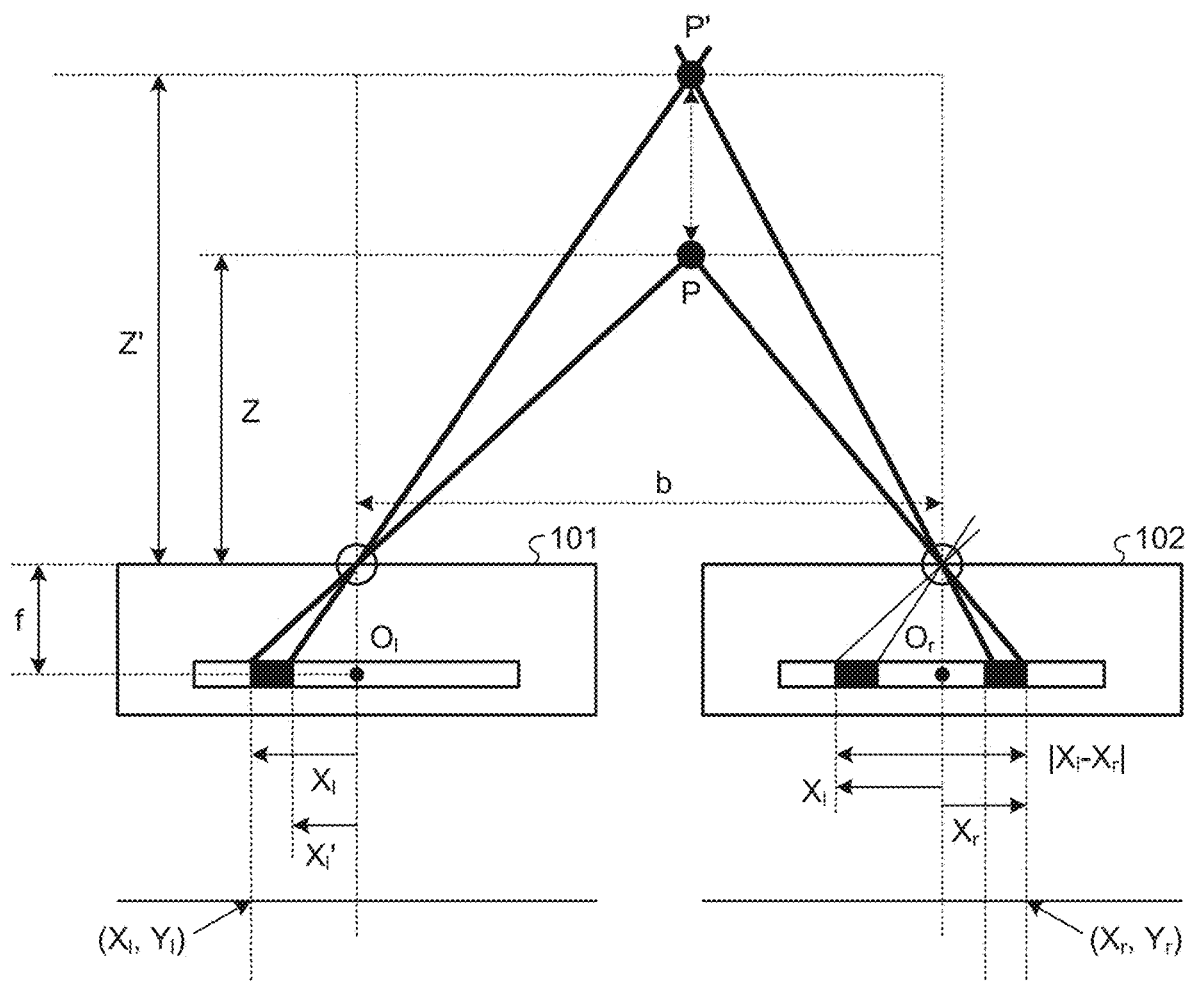
FIG. 6 is a diagram for explaining a method of measuring a distance in a depth direction by using a stereo camera.

FIG. 6 is a diagram for explaining the method of measuring the distance in the depth direction using the stereo camera. As illustrated in FIG. 6, two cameras 101 and 102 are arranged with a baseline length b. Further, a distance between a measurement target point P and the cameras 101 and 102 is denoted by Z. Furthermore, a focal length of the cameras 101 and 102 is denoted by f.

A three-dimensional coordinate of the distance measurement target point P is represented by (Pxl, Pyl, Pzl) when the coordinate system of the left camera 101 is used as an origin, and represented by (Pxr, Pyr, Pzr) when the coordinate system of the right camera 102 is used as an origin.

The coordinates systems of the left camera 101 and the right camera 102 are shifted parallel to each other by the baseline length b in an x-axis direction, and therefore represented by Equation (1) below.

$$Pxr = Pxl - b$$

$$Pyr = Pyl$$

$$Pzr = Pzl \qquad (1)$$

A point at which the distance measurement target point P is imaged is represented by Equations (2) and (3) below using similar triangles assuming that the point is represented by (Xl, Yl) on the coordinates on an image of the left camera 101 and represented by (Xr, Yr) on the coordinates on an image of the right camera 102.

$$Xl = f \cdot Pxl/Pzl \qquad (2)$$

$$Xr = f \cdot Pxr/Pzr \qquad (3)$$

According to Equations (1), (2), and (3), parameters related to the three-dimensional coordinate of the distance measurement target point P are eliminated, and the distance Z between the distance measurement target point P and the cameras 101 and 102 can be represented by Equation (4) below.

$$Z = f \cdot b/(Xl - Xr) \qquad (4)$$

Accordingly, the distance Z from the two cameras 101 and 102 to the distance measurement target point P in the depth direction can be represented by the focal length f, the baseline length b, and disparity (Xl−Xr). In other words, by detecting the disparity between the points P in the obtained two images, it is possible to obtain the distance Z between the distance measurement target point P and the cameras 101 and 102.

Next, a distance measurement error of the stereo camera will be described.

Assuming that a minute read error Δdx exists between a true value dx and an actual measurement value dx' of disparity in the images, dx is represented as follows.

$$dx = dx' + \Delta dx$$

If it is assumed that a true value of the distance from the two cameras 101 and 102 to the distance measurement target point P is denoted by Z, and a distance from the cameras 101 and 102 to the distance measurement target point P' calculated from the disparity read from the images is denoted by Z', a distance measurement error ΔZ in the depth direction is represented by Equation (5) below based on Equation (4).

$$\begin{aligned}\Delta Z &= Z' - Z \\ &= f \cdot b/dx' - f \cdot b/dx \\ &= f \cdot b/dx' - f \cdot b/(dx' + \Delta dx) \\ &= (f \cdot b/dx'(dx' + \Delta dx)) \cdot \Delta dx \\ &= (f \cdot b/dx') \cdot (f \cdot b/(dx' + \Delta dx)) \cdot (\Delta dx/(f \cdot b)) \\ &= Z \cdot Z' \cdot (\Delta dx/(f \cdot b)) \\ &= (Z^2/(f \cdot b)) \cdot \Delta dx\end{aligned} \qquad (5)$$

Therefore, the distance measurement error ΔZ in the depth direction obtained from the stereo image is proportional to the square of the distance Z from the two cameras 101 and 102 to the distance measurement target point P and is inversely proportional to the baseline length b.

Next, resolution of the distance in the depth direction obtained by the stereo camera will be described.

Minimum resolution of an image is one pixel. If it is assumed that an error of ±1 pixel exists between the distance measurement target points P in the left image and the right image, the following equation is obtained, where a pixel size is represented by (px, py).

$$Xl' = Xl + px$$

$$Xr' = Xr - px$$

Therefore, a distance Z" between a point P', which is calculated from the disparity including the pixel read error, and the two cameras 101 and 102 are represented as follows based on Equation (4).

$$\begin{aligned}Z'' &= f \cdot b/((X1 + px) - (Xr - px)) \\ &= f \cdot b/(X1 - Xr + 2px)\end{aligned}$$

In other words, a size |Z"−Z| of an image read error is represented as follows.

$$|Z''-Z| = |f \cdot b/(Xl - Xr + 2px) - f \cdot b(Xl - Xr)|$$

The above-described equation corresponds to a case where dx'=Xl−Xr and Δdx=−2px are applied to Equation (5). Thus, the following Equation (6) is given based on Equation (5).

$$|\Delta Z| = |(Z^2/(f \cdot b)) \cdot (-2px)| \qquad (6)$$

Next, the method of measuring the distance in the depth direction by using the camera 51 provided in the image acquisition apparatus 5 of the present embodiment will be described.

FIG. 7 is a diagram for explaining the method of measuring the distance in the depth direction using the camera 51 included in the image acquisition apparatus 5. As illustrated in FIG. 7, a distance measurement target point Pd is provided on a surface of the dewar 2, and a distance measurement target point Ph is provided on a surface of the head of the subject 10. As illustrated in FIG. 7, a focal length of the camera 51 is denoted by f.

When the coordinate system of the camera 51 is used as an origin, the three-dimensional coordinate of the distance measurement target point Pd is represented by (Xd, Yd, Zdc), and the three-dimensional coordinate of the distance measurement target point Ph is represented by (Xh, Yh, Zhc). Further, it is assumed that points, at which the distance measurement target point Pd and the distance measurement target point Ph are imaged, are represented by Pd(xd, yd) and Ph(xh, yh) on the coordinates in the image. Based on a principle of similar triangles, a distance Zdc between the distance measurement target point Pd and the camera 51 and a distance Zhc between the distance measurement target point Ph and the camera 51 are represented by Equations (7) and (8) below.

$$Zdc=(Xd/xd) \cdot f \quad (7)$$

$$Zhc=(Xh/xh) \cdot f \quad (8)$$

Here, if an angle between the coordinate system of the camera 51 and the coordinate system of the dewar 2 is obtained, Xd is known based on three-dimensional shape data of the dewar 2. The angle between the coordinate system of the camera 51 and the coordinate system of the dewar 2 is a value that can be calculated by detecting, from the image, positional relationships between at least three points that are extracted from the three-dimensional shape data of the dewar 2.

Similarly, Xh is known based on the three-dimensional shape data of the head of the subject 10 when an angle between the coordinate system of the camera 51 and the coordinate system of the head of the subject 10 is obtained. The angle between the coordinate system of the camera 51 and the coordinate system of the head of the subject 10 is a value that can be calculated by detecting, from the image, positional relationships between at least three points that are extracted from three-dimensional shape data of the head of the subject 10.

In summary, in Equations (7) and (8), Xd and Xh are known values, and the distance Zhc between the distance measurement target point Ph and the camera 51 and the distance Zdc between the distance measurement target point Pd and the camera 51 can be calculated by detecting xd and xh in the image.

Next, a distance measurement error in the depth direction using the camera 51 included in the image acquisition apparatus 5 will be described.

Assuming that a minute read error Δxd arises between a true value xd and an actual measurement value xd' of the x-coordinate of the distance measurement target point Ph on the surface of the head of the subject 10 in the image, xd is represented as follows.

$$xd=xd'+\Delta xd$$

Further, assuming that a true value of a distance from the camera 51 to the distance measurement target point Pd on the surface of the dewar 2 is denoted by Zdc, and a distance from the camera 51 to the distance measurement target point Pd read from the image is denoted by Zdc', a distance measurement error ΔZdc in the depth direction is represented as follows based on Equation (7).

$$\Delta Zdc = Zdc' - Zdc$$
$$= (Xd/xd') \cdot f - (Xd/xd) \cdot f$$
$$= f \cdot Xd/xd' - f \cdot Xd/(xd' + \Delta xd)$$

The above-described equation corresponds to Equation (5) in a case where b is replaced with Xd, dx' is replaced with xd', and Δdx is replaced with Δxd, and therefore represented by Equation (9) below based on Equation (5).

$$\Delta Zdc \approx (Zdc^2/(f \cdot Xd)) \cdot \Delta xd \quad (9)$$

Accordingly, the distance measurement error ΔZdc in the depth direction obtained by the image acquisition apparatus 5 is proportional to the square of the distance from the camera 51 to the distance measurement target point Pd on the surface of the dewar 2 and is inversely proportional to the x-coordinate in the three-dimensional coordinate system of the dewar 2.

Next, resolution of the distance in the depth direction obtained by the camera 51 included in the image acquisition apparatus 5 will be described.

In the stereo camera described above, because the stereo camera includes the two cameras, even if a read error of a single camera is one pixel, a read error of two pixels occurs at maximum in the two cameras. In contrast, in the single camera, a read error is one pixel at maximum.

In the case of the camera 51 included in the image acquisition apparatus 5, the resolution is obtained by replacing Δxd with a pixel size px in Equation (9). Therefore, according to Equation (9), the distance measurement error ΔZdc in the depth direction can be represented by Equation (10) below.

$$\Delta Zdc \approx (Zdc^2/(f \cdot Xd)) \cdot px \quad (10)$$

The distance measurement errors ΔZdc in the depth direction and the resolution in both of the stereo camera and the single camera will be compared based on specific values.

In this example, a distance between the camera and the distance measurement target object is set to Z=900 millimeters (mm). Further, a condition in which an image of an area corresponding to a width of 200 mm in a horizontal direction of the subject is acquired so that the the dewar 2 and the head of the subject 10 can be included in the image.

Furthermore, assuming that an image sensor of the camera is a 1/3-type (4.8 mm in the horizontal direction×3.6 mm in the vertical direction) and the number of pixels is about two million (1920×1080), a width of a single pixel is 2.5 micrometers (μm). Therefore, if an image of the area of 200 mm in the horizontal direction is to be obtained from a position that is separated by Z=900 mm from the distance measurement target object, the focal length f=21.6 mm.

Under the conditions described above, if the baseline length of the stereo camera is set to 50 mm and a read error of the disparity is ±1 pixel, the distance measurement error ΔZ is represented as follows based on Equation (5).

$$\Delta Z \approx (Z^2/(f \cdot b)) \cdot \Delta dx$$

$$\approx 4 \text{ mm}$$

Furthermore, the resolution is represented as follows based on Equation (6).

$$|\Delta Z| \approx |(Z^2/(f \cdot b)) \cdot (-2px)|$$

$$\approx 4 \text{ mm}$$

In the stereo camera, a matching error also occurs in the disparity in a process of searching for identical feature points in the two images, so that the distance measurement error and the resolution are further reduced.

In contrast, the distance measurement error ΔZdc in the camera 51 included in the image acquisition apparatus 5 is, at the point Pd where Xd=50 mm on the surface of the dewar 2, represented as follows based on Equation (9).

$$\Delta Zdc \approx (Zdc^2/(f \cdot Xd)) \cdot \Delta xd$$
$$\approx 2 \text{ mm}$$

Furthermore, the resolution is represented as follows based on Equation (10).

$$\Delta Zdc \approx (Zdc^2/(f \cdot Xd)) \cdot px$$
$$\approx 2 \text{ mm}$$

As described above, even in the single camera 51 included in the image acquisition apparatus 5, it is possible to accurately detect the distance in the depth direction by providing the three-dimensional shape data of the dewar 2 and the three-dimensional shape data of the subject 10.

Figure 8:
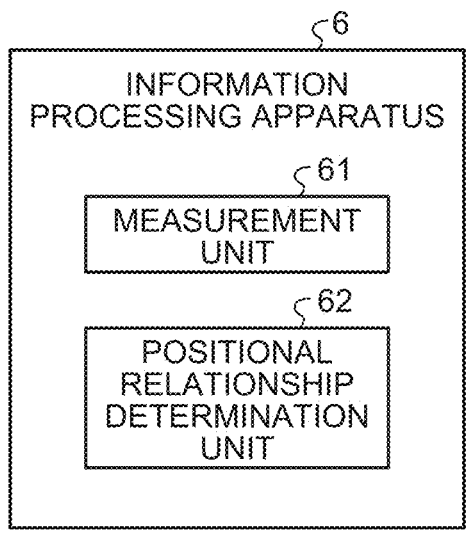
FIG. 8 is a diagram for explaining functions of the information processing apparatus.

Next, a characteristic function among the functions of the information processing apparatus 6 of the present embodiment will be described. FIG. 8 is a diagram for explaining functions of the information processing apparatus 6.

The information processing apparatus 6 includes a measurement unit 61 and a positional relationship determination unit 62 serving as means for determining a positional relationship.

The measurement unit 61 and the positional relationship determination unit 62 are implemented by causing the arithmetic processing device 26 to read and execute the biological information measurement program that is stored in the auxiliary storage device 24, the memory device 25, or the like.

The measurement unit 61 measures brain neural activity of the subject based on biological signals (magnetoencephalography signals) that are detected through the magnetic sensors 1 by giving stimuli.

The positional relationship determination unit 62 makes positional relationships between the plurality of head reference points and the dewar 2. The positional relationship determination unit 62 determines positional relationships between the head reference points of the head of the subject 10 and the magnetic sensors 1 in the three-dimensional space based on the dewar structural data related to the positions and the postures of the magnetic sensors 1. In the present embodiment, the dewar structural data is three-dimensional arrangement data of the magnetic sensors 1.

Further, the positional relationship determination unit 62 detects a change in the position of the head of the subject 10 based on images that are captured by the camera 51 (imaging device) at different times, and re-determines the positional relationships between the reference points of the subject 10 and the magnetic sensors 1. More specifically, the positional relationship determination unit 62 determines the positional relationships between the head reference points of the head of the subject 10 and the magnetic sensors 1 based on detection values of the magnetic sensors 1 that detect magnetic fields generated by the marker coils and the three-dimensional arrangement data of the magnetic sensors 1. It is preferable that the reference points are located at positions closer to the dewar in the head of the subject (for example, a face of the subject).

First, a process of determining the positional relationships between the dewar 2 and the head reference points (seals S1, S2, and S3) by the information processing apparatus 6 will be described.

Figure 9:
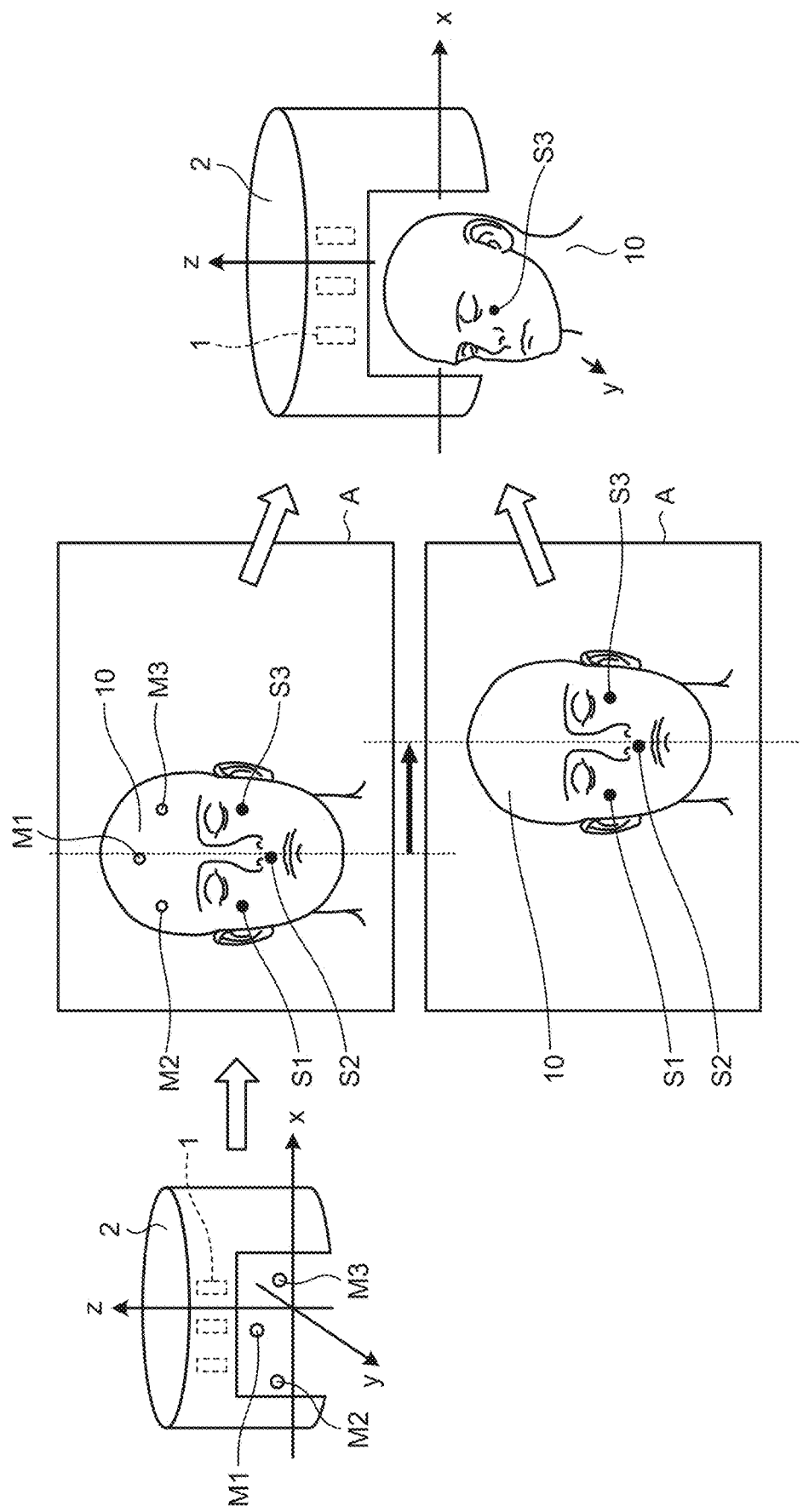
FIG. 9 is a diagram schematically illustrating a process performed by the information processing apparatus.

FIG. 9 is a diagram schematically illustrating a process performed by the information processing apparatus 6. The positional relationship determination unit 62 of the information processing apparatus 6 acquires an image A including the head reference points (seals S1, S2, and S3) and the dewar 2 (not shown in the image A in FIG. 9) from the image acquisition apparatus 5. The positional relationship determination unit 62 then calculates positional relationships between the dewar 2 and the head reference points (seals S1, S2, and S3) in the image A.

Subsequently, the positional relationship determination unit 62 of the information processing apparatus 6 calculates head reference points at which relationships between a shape of the dewar 2 and the head reference points (seals S1, S2, and S3) in the three-dimensional space correspond to the above-described positional relationships.

The positional relationship determination unit 62 of the information processing apparatus 6 determines the positional relationships in the three-dimensional space between the head reference points (seals S1, S2, and S3) and the magnetic sensors 1 based on the pre-provided three-dimensional arrangement data of the magnetic sensors 1.

Magnetic measurement on the head of the subject 10 is performed immediately after the process described above.

Next, a relative position change amount acquisition process, which is performed by the information processing apparatus 6, will be described. The positional relationship determination unit 62 of the information processing apparatus 6 acquires a relative position change amount based on a measurement direction and positions of the dewar 2 and the head of the subject 10 at the time of measurement while the brain function measurement apparatus 3 measures magnetoencephalography or the like.

When acquiring the relative position change amount, the positional relationship determination unit 62 of the information processing apparatus 6 acquires magnetic fields generated by the marker coils M1, M2, and M3, which are detected by the magnetic sensors 1, and simultaneously acquires the image A including the head reference points (seals S1, S2, and S3) and the marker coils (magnetic generators) M1, M2, and M3 of the subject 10 from the image acquisition apparatus 5. If the subject is an infant, he/she tends to refuse to attach the marker coils or the like. In the present disclosure, it is allowed to remove the marker coils after finishing measuring positions with the marker coils.

Subsequently, the positional relationship determination unit 62 of the information processing apparatus 6 acquires the image A including the head reference points (seals S1, S2, and S3) at a different time from the time of the above-described process. The positional relationship determination unit 62 then detects a positional change of the head reference points (seals S1, S2, and S3) from those of the previously-obtained image A, that is, a positional change of the head of the subject 10.

Therefore, even if the subject 10 moves, the positional change of the head of the subject 10 after the movement is detected. Thus, the information processing apparatus 6 is able to accurately determine the positional relationship of the head of the subject 10 in the three-dimensional space of the dewar 2.

In this manner, according to the first embodiment, it is possible to acquire an image for correcting the position of the head by using the single imaging device. Further, it is possible to determine the positional relationship between the head of the subject and the dewar in real time with high accuracy and simultaneously measure brain neural activity in the whole head, without reducing the accuracy in defining a position in the image depth direction.

Second Embodiment

A second embodiment will be described below.

The second embodiment is different from the first embodiment in that the shape of the dewar 2 and the three-dimensional arrangement data of the magnetic sensors 1 are used as the dewar structural data. In the second embodiment described below, explanation of the same components as those of the first embodiment will be omitted and only a difference from the first embodiment will be described.

The information processing apparatus 6 according to the foregoing first embodiment is configured to determine, by using the three-dimensional arrangement data of the magnetic sensors 1 as the dewar structural data, the positional relationships between the head of the subject 10 and the magnetic sensors 1 based on the detection values of the magnetic sensors 1 that detect magnetic fields generated by the marker coils.

In contrast, the information processing apparatus 6 according to the present second embodiment uses the shape of the dewar 2 and the three-dimensional arrangement data of the magnetic sensors 1 as the dewar structural data in order to determine the positional relationships between the head of the subject 10 and the magnetic sensors 1.

Figure 10:
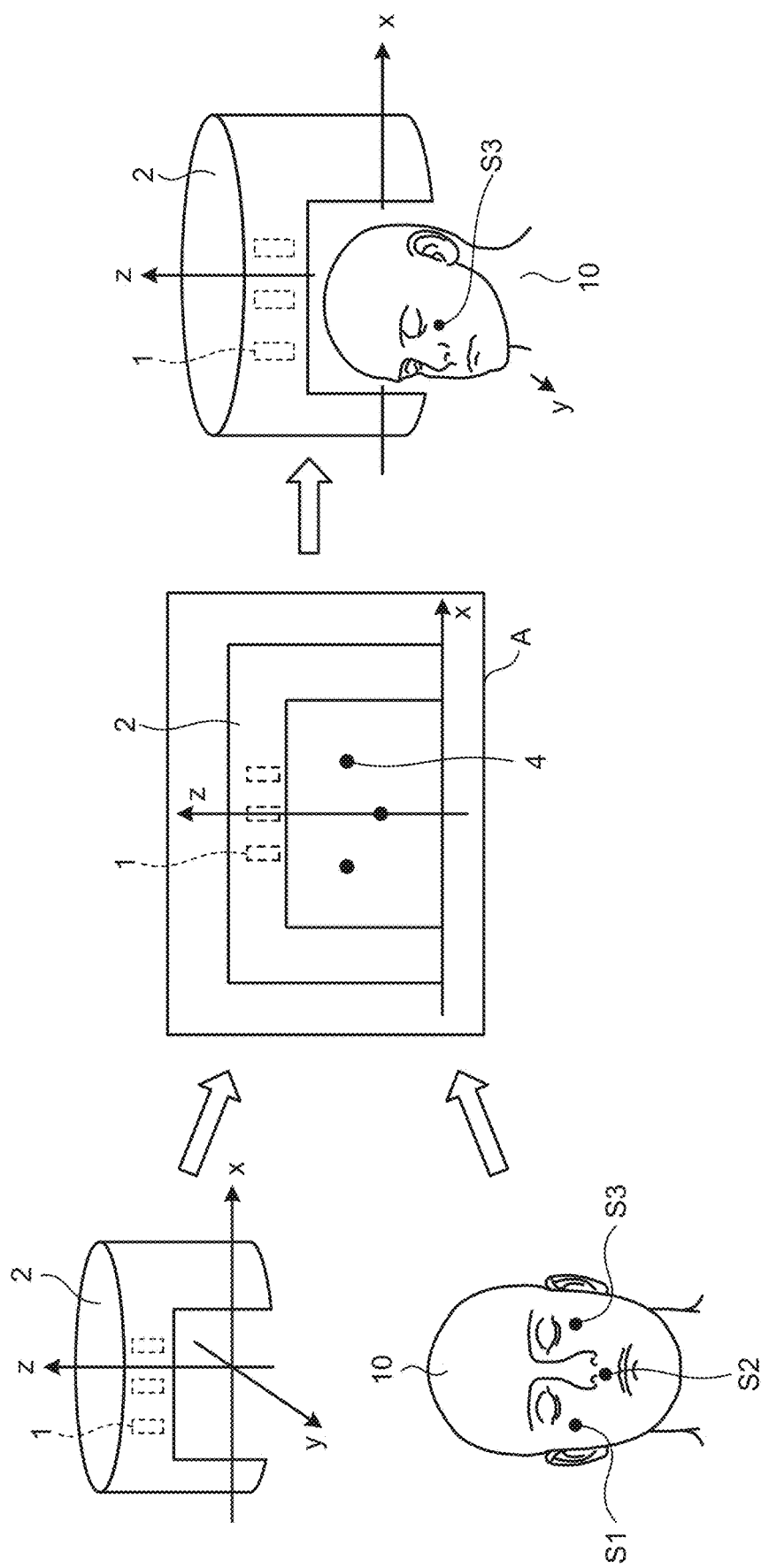
FIG. 10 is a diagram schematically illustrating a process performed by an information processing apparatus according to a second embodiment.

FIG. 10 is a diagram schematically illustrating a process performed by the information processing apparatus 6 according to the second embodiment. A process of determining the positional relationships between the dewar 2 and the head reference points (seals S1, S2, and S3) by the information processing apparatus 6 will be described.

As illustrated in FIG. 10, the positional relationship determination unit 62 of the information processing apparatus 6 acquires from the image acquisition apparatus 5 an image A in which the head reference points (seals S1, S2, and S3) and the dewar 2 are captured, and calculates the positional relationships between the dewar 2 and the head reference points (seals S1, S2, and S3) in the image A.

Subsequently, the positional relationship determination unit 62 of the information processing apparatus 6 calculates head reference points at which relationships between the shape of the dewar 2 and the head reference points (seals S1, S2, and S3) in the three-dimensional space correspond to the above-described positional relationships.

The positional relationship determination unit 62 of the information processing apparatus 6 determines the positional relationships in the three-dimensional space between the head reference points (seals S1, S2, and S3) and the magnetic sensors 1 based on the pre-provided shape of the dewar 2 and the pre-provided three-dimensional arrangement data of the magnetic sensors 1.

Further, the positional relationship determination unit 62 of the information processing apparatus 6 calculates relative position change amounts among the magnetic sensors 1 and the head reference points (seals S1, S2, and S3) based on a positional change of the head reference points (seals S1, S2, and S3) between two different times.

In this manner, according to the second embodiment, by providing, in advance, relative positional relationship data of the head reference points of the head of the subject 10 and the shape of the dewar 2 in the three-dimensional space, it is possible to determine the positional relationship between the head of the subject and the dewar in real time with high accuracy, and simultaneously measure brain neural activity in the whole head based on images that are acquired during measurement of brain neural activity, without reducing the accuracy in defining a position in the image depth direction.

Third Embodiment

A third embodiment will be described below.

The third embodiment is different from the first embodiment and the second embodiment in that the image acquisition apparatus 5 acquires a three-dimensional shape image in which the dewar 2 and the head reference points of the subject 10 are captured. In the third embodiment described below, explanation of the same components as those of the first embodiment or the second embodiment will be omitted and only a difference from the first embodiment or the second embodiment will be described.

The image acquisition apparatus 5 according to the foregoing first embodiment is configured to capture a two-dimensional image of the head of the subject 10. In contrast, the image acquisition apparatus 5 according to the present third embodiment is capable of acquiring a three-dimensional shape image including the dewar 2 and the head reference points of the subject 10.

Figure 11:
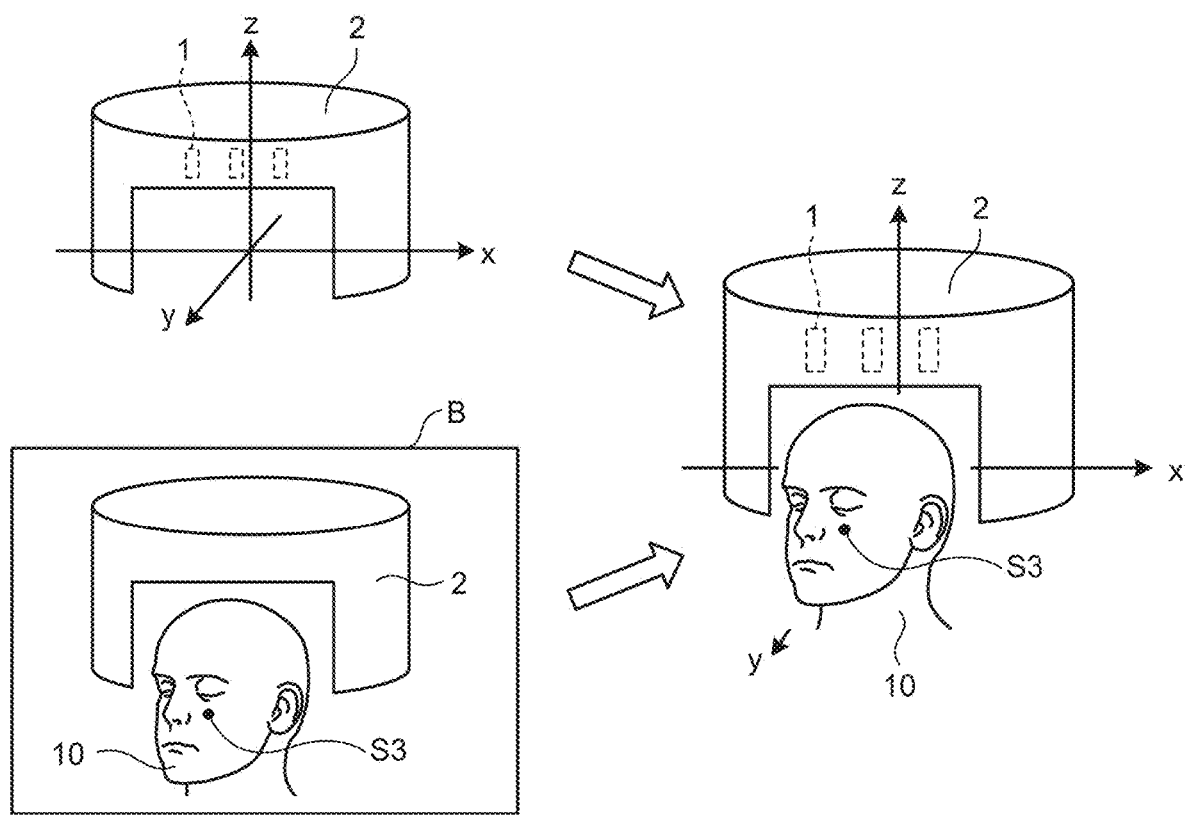
FIG. 11 is a diagram schematically illustrating a process performed by an information processing apparatus according to a third embodiment.

FIG. 11 is a diagram schematically illustrating a process performed by the information processing apparatus 6 according to the third embodiment. As illustrated in FIG. 11, the information processing apparatus 6 first acquires, from the image acquisition apparatus 5, a three-dimensional image B in which the dewar 2 and the head reference points on the head of the subject 10 are captured.

Subsequently, the positional relationship determination unit 62 of the information processing apparatus 6 makes positional relationships between the head reference points (seals S1, S2, and S3) and the dewar 2 in three-dimensional head shape data of the subject 10, based on the image that is acquired by the the image acquisition apparatus 5 and that includes the three-dimensional head shape data of the subject 10 and the three-dimensional shape data of the dewar 2.

The positional relationship determination unit 62 of the information processing apparatus 6 determines the positional relationships in the three-dimensional space between the head reference points (seals S1, S2, and S3) and the magnetic sensors 1 based on the pre-provided shape of the dewar 2 as the dewar structural data and the pre-provided three-dimensional arrangement data of the magnetic sensors 1.

Furthermore, the positional relationship determination unit 62 of the information processing apparatus 6 calculates relative position change amounts among the magnetic sensors 1 and the head reference points (seals S1, S2, and S3) based on a positional change of the head reference points (seals S1, S2, and S3) between images that are acquired by the imaging device at different times.

Therefore, it is possible to determine the positional relationship of the head in the three-dimensional space of the dewar 2.

According to the present disclosure, it is possible to acquire an image for correcting a position of a head by using a single imaging device.

The above-described embodiments are illustrative and do not limit the present invention. Thus, numerous additional modifications and variations are possible in light of the above teachings. For example, at least one element of different illustrative and exemplary embodiments herein may be combined with each other or substituted for each other within the scope of this disclosure and appended claims. Further, features of components of the embodiments, such as the number, the position, and the shape are not limited the embodiments and thus may be preferably set. It is therefore to be understood that within the scope of the appended claims, the disclosure of the present invention may be practiced otherwise than as specifically described herein.

Further, any of the above-described apparatus, devices or units can be implemented as a hardware apparatus, such as a special-purpose circuit or device, or as a hardware/software combination, such as a processor executing a software program.

Further, as described above, any one of the above-described and other methods of the present invention may be embodied in the form of a computer program stored in any kind of storage medium. Examples of storage mediums include, but are not limited to, flexible disk, hard disk, optical discs, magneto-optical discs, magnetic tapes, non-volatile memory, semiconductor memory, read-only-memory (ROM), etc.

Alternatively, any one of the above-described and other methods of the present invention may be implemented by an application specific integrated circuit (ASIC), a digital signal processor (DSP) or a field programmable gate array (FPGA), prepared by interconnecting an appropriate network of conventional component circuits or by a combination thereof with one or more conventional general purpose microprocessors or signal processors programmed accordingly.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA) and conventional circuit components arranged to perform the recited functions.

What is claimed is:

1. A biological information measurement system comprising:
   a dewar covering a head of a subject and containing a plurality of sensors that are arranged for detecting biological signals;
   a single imaging device configured to acquire an image in which three or more reference points and the dewar are captured, the reference points being set in relation to the subject;
   a memory; and
   a hardware processor coupled to the memory, the hardware processor being configured to:
      measure brain neural activity of the subject based on the biological signals detected by the plurality of sensors;
      determine positional relationships between the reference points of the subject and the plurality of sensors based on the reference points and positional relationship data of the dewar; and
      re-determine the positional relationships between the reference points of the subject and the plurality of sensors, based on images that are acquired by the single imaging device at different times.

2. The biological information measurement system according to claim 1, further comprising three or more magnetic generators arranged on the subject, wherein
   the positional relationship data of the dewar is data representing positions at which the plurality of sensors are arranged, and
   the hardware processor is configured to perform the determination on the positional relationships between the reference points of the subject and the plurality of sensors, based on
      detection values of magnetic fields generated by the magnetic generators, the detection values being detected by the plurality of sensors, and
      the data representing the positions at which the plurality of sensors are arranged.

3. The biological information measurement system according to claim 1, wherein
   the positional relationship data of the dewar is data representing a shape of the dewar and positions at which the plurality of sensors are arranged, and
   the hardware processor is configured to:
      make, based on the image, positional relationships between the reference points and the dewar; and
      determine positional relationships between the reference points of the subject and the plurality of sensors in a three-dimensional space by using the data representing the shape of the dewar and the positions at which the plurality of sensors are arranged.

4. The biological information measurement system according to claim 1, wherein
   the single imaging device is capable of acquiring a three-dimensional shape image,
   the positional relationship data of the dewar is data representing a shape of the dewar and positions at which the plurality of sensors are arranged, and
   the hardware processor is configured to:
      make positional relationships between the reference points and the dewar in three-dimensional head shape data of the subject, based on an image that is acquired by the single imaging device and that includes the three-dimensional head shape data of the subject and three-dimensional shape data of the dewar; and
      determine positional relationships in a three-dimensional space between the reference points of the subject and the plurality of sensors, based on the data representing the shape of the dewar and the positions at which the plurality of sensors are arranged.

5. The biological information measurement system according to claim 1, wherein the reference points are feature points of a head of the subject.

6. The biological information measurement system according to claim 1, wherein the reference points are each provided with a mark having a known dimension that allows the single imaging device to capture the mark on the image.

7. The biological information measurement system according to claim 1, wherein the reference points are provided on skin over any of a maxilla bone, a frontal bone, a nasal bone, a zygomatic bone, and a temporal bone.

8. A non-transitory computer-readable recording medium on which an executable program is recorded, the program giving an instruction to a hardware processor of a biological information measurement system that includes a dewar covering a head of a subject and containing a plurality of sensors that are arranged for detecting biological signals and includes a single imaging device configured to acquire an image in which three or more reference points and the dewar are captured, the reference points being set in relation to the subject, the instruction causing the hardware processor to:
- measure brain neural activity of the subject based on the biological signals detected by the plurality of sensors;
- determine positional relationships between the reference points of the subject and the plurality of sensors based on the reference points and positional relationship data of the dewar; and
- re-determine the positional relationships between the reference points of the subject and the plurality of sensors, based on images that are acquired by the single imaging device at different times.

9. The non-transitory computer-readable recording medium according to claim 8, wherein the biological information measurement system further includes three or more magnetic generators arranged on the subject, wherein
- the positional relationship data of the dewar is data representing positions at which the plurality of sensors are arranged, and
- the instruction further causes the hardware processor to perform the determination on the positional relationships between the reference points of the subject and the plurality of sensors, based on
  - detection values of magnetic fields generated by the magnetic generators, the detection values being detected by the plurality of sensors, and
  - the data representing the positions at which the plurality of sensors are arranged.

10. The non-transitory computer-readable recording medium according to claim 8, wherein
- the positional relationship data of the dewar is data representing a shape of the dewar and positions at which the plurality of sensors are arranged, and
- the instruction further causes the hardware processor to:
  - make, based on the image, positional relationships between the reference points and the dewar; and
  - determine positional relationships between the reference points of the subject and the plurality of sensors in a three-dimensional space by using the data representing the shape of the dewar and the positions at which the plurality of sensors are arranged.

11. The non-transitory computer-readable recording medium according to claim 8, wherein
- the single imaging device is capable of acquiring a three-dimensional shape image,
- the positional relationship data of the dewar is data representing a shape of the dewar and positions at which the plurality of sensors are arranged, and
- the instruction further causes the hardware processor to:
  - make positional relationships between the reference points and the dewar in three-dimensional head shape data of the subject, based on an image that is acquired by the single imaging device and that includes the three-dimensional head shape data of the subject and three-dimensional shape data of the dewar; and
  - determine positional relationships in a three-dimensional space between the reference points of the subject and the plurality of sensors, based on the data representing the shape of the dewar and the positions at which the plurality of sensors are arranged.

12. The non-transitory computer-readable recording medium according to claim 8, wherein the reference points are feature points of a head of the subject.

13. The non-transitory computer-readable recording medium according to claim 8, wherein the reference points are each provided with a mark having a known dimension that allows the single imaging device to capture the mark on the image.

14. The non-transitory computer-readable recording medium according to claim 8, wherein the reference points are provided on skin over any of a maxilla bone, a frontal bone, a nasal bone, a zygomatic bone, and a temporal bone.

15. The non-transitory computer-readable recording medium according to claim 8, wherein the instruction further causes the hardware processor to:
- determine distances from the single imaging device to the reference points of the subject based on three-dimensional head shape data of the subject and three-dimensional shape data of the dewar; and
- determine the positional relationships between the reference points of the subject and the plurality of sensors based on the determined distances.

16. The non-transitory computer-readable recording medium according to claim 8, wherein the instruction further causes the hardware processor to:
- determine a relative position change of the subject based on the images that are acquired by the single imaging device at different times.

17. The non-transitory computer-readable recording medium according to claim 16, wherein the instruction further causes the hardware processor to:
- correct the position of the subject based on the determined relative position change.

18. The biological information measurement system according to claim 1, wherein the hardware processor is further configured to:
- determine distances from the single imaging device to the reference points of the subject based on three-dimensional head shape data of the subject and three-dimensional shape data of the dewar; and
- determine the positional relationships between the reference points of the subject and the plurality of sensors based on the determined distances.

19. The biological information measurement system according to claim 1, wherein the hardware processor is further configured to:
- determine a relative position change of the subject based on the images that are acquired by the single imaging device at different times.

20. The biological information measurement system according to claim 19, wherein the hardware processor is further configured to:
- correct the position of the subject based on the determined relative position change.

* * * * *

UNITED STATES PATENT AND TRADEMARK OFFICE
CERTIFICATE OF CORRECTION

PATENT NO. : 11,439,336 B2
APPLICATION NO. : 16/589695
DATED : September 13, 2022
INVENTOR(S) : Yoshihiro Misaka et al.

It is certified that error appears in the above-identified patent and that said Letters Patent is hereby corrected as shown below:

On the Title Page

Column 1, item (30) insert:
--Foreign Application Priority Data
(30)     Oct. 2, 2018     (JP).......................... 2018-187819
             Apr. 25, 2019     (JP).......................... 2019-084725--

Signed and Sealed this
Twenty-sixth Day of December, 2023

Katherine Kelly Vidal
*Director of the United States Patent and Trademark Office*